(12) United States Patent
Kinsho et al.

(10) Patent No.: US 6,291,696 B2
(45) Date of Patent: Sep. 18, 2001

(54) PREPARATION OF TRIS (TRIMETHYLSILYL) SILYLETHYL ESTERS

(75) Inventors: Takeshi Kinsho; Koji Hasegawa; Takeru Watanabe; Tohru Kubota; Ayumu Kiyomori, all of Nakakubiki-gun (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/754,320

(22) Filed: Jan. 5, 2001

(30) Foreign Application Priority Data

Jan. 6, 2000 (JP) .................................................. 00-000888

(51) Int. Cl.$^7$ ....................................................... C07F 7/08
(52) U.S. Cl. .............................................................. 556/440
(58) Field of Search ............................................... 556/440

(56) References Cited

U.S. PATENT DOCUMENTS

| | | | |
|---|---|---|---|
| 4,946,977 | * 8/1990 | Bernhardt et al. | .................... 556/440 |
| 5,646,325 | * 7/1997 | Monkiewicz et al. | ................ 556/440 |
| 5,985,524 | 11/1999 | Allen et al. . | |
| 6,118,015 | * 9/2000 | Haas et al. | ............................ 556/440 |

OTHER PUBLICATIONS

Sooriyakumaran et al., "Positive Bilayer Resists for 248 and 193 nm Lithography," *SPIE*, vol. 3333, pp. 219–227.

Brook et al., "A New Anlon Rearrangement Involving Silyl Migration to Oxygen," *Organometallics*, vol. 3, pp. 1317–1318 (1984).

Kopping et al., "(Me$_s$Si)$_3$SiH: An Efficient Hydrosilylating Agent of Alkenes and Alkynes," *J. Org. Chem.*, vol. 57, p. 3994–4000 (1992).

* cited by examiner

Primary Examiner—Paul F. Shaver
(74) *Attorney, Agent, or Firm*—Millen, White, Zelano & Branigan PC

(57) ABSTRACT

An industrially acceptable process for preparing 2-[tris (trimethylsilyl)silyl]ethyl (meth)acrylate in high yields involves reacting 2-[tris(trimethylsilyl)silyl]ethyl acetate with an alcohol in the presence of a catalyst to form 2-[tris(trimethylsilyl)silyl]ethanol, then reacting it with a (meth)acrylate ester.

11 Claims, No Drawings

PREPARATION OF TRIS (TRIMETHYLSILYL) SILYLETHYL ESTERS

This invention relates to a process for preparing 2-[tris(trimethylsilyl)silyl]ethyl methacrylate and 2-[tris(trimethylsilyl)silyl]ethyl acrylate. For brevity sake, methacrylate and acrylate are collectively designated (meth)acrylate.

BACKGROUND OF THE INVENTION

2-[Tris(trimethylsilyl)silyl]ethyl (meth)acrylate is a useful monomer to form a polymer for use in bi-layer photoresist to be processed by lithography using excimer laser light. In the prior art, 2-[tris(trimethylsilyl)silyl]ethyl methacrylate is prepared by an esterification process of reacting a corresponding alcohol, that is, 2-tris(trimethylsilyl)silylethanol with methacryloyl chloride (see Sooriyakumaran et al., SPIE, Vol. 3333, p. 219 and Allen et al., U.S. Pat. No. 5,985,524). The process starting from the acid chloride and the alcohol in these references, however, has the following problems when it is carried out on an industrial scale. The reaction is usually effected using more than an equivalent of a base in a solvent. The acid chloride should be handled with caution since it is corrosived moisture sensitive. Work-up process, including extraction and concentration step, is necessarily required.

On the other hand, 2-[tris(trimethylsilyl)silyl]ethanol is synthesized by reaction of a silicon metal reagent, tris(trimethylsilyl)silyllithium with low-boiling ethylene oxide (boiling point 10.7° C.) (see Brook et al., Organometallics, 1984, 3, p. 1317). This synthesis process also encounters difficulty upon industrial implementation because the awkward-to-handle compound is used.

Also known in the art is the synthesis of 2-[tris(trimethylsilyl)silyl]ethyl acetate by reaction of tris(trimethylsilyl)silane with vinyl acetate (see Kopping et al., J. Org. Chem., 1992, 57, p. 3994). It is also contemplated to synthesize 2-[tris(trimethylsilyl)silyl]ethanol by hydrolyzing or reducing the 2-[tris(trimethylsilyl)silyl]ethyl acetate. Another known example is reduction with lithium aluminum hydride (see Allen et al., U.S. Pat. No. 5,985,524). This process, however, encounters more difficulty because two steps of alcohol formation and esterification reaction are involved.

Another problem is that the intermediate 2-[tris(trimethylsilyl)silyl]ethanol is impossible to purify by distillation since it is a crystal having a melting point of about 150° C. Purification by recrystallization is industrially troublesome, and a substantial loss is inevitable.

SUMMARY OF THE INVENTION

An object of the invention is to provide a novel and improved process for preparing 2-[tris(trimethylsilyl)silyl]ethyl methacrylate and 2-[tris(trimethylsilyl)silyl]ethyl acrylate in high yields using 2-[tris(trimethylsilyl)silyl]ethyl acetate as a starting material, the process being easy and safe to carry out on an industrial scale.

It has been found that 2-[tris(trimethylsilyl)silyl]ethyl (meth)acrylate can be prepared simply by reacting 2-[tris(trimethylsilyl)silyl]ethyl acetate with an alcohol in the presence of a catalyst, then reacting the resulting 2-[tris(trimethylsilyl)silyl]ethanol with a (meth)acrylate ester.

The invention provides a process for preparing 2-[tris(trimethylsilyl)silyl]ethyl (meth)acrylate, comprising the steps of reacting 2-[tris(trimethylsilyl)silyl]ethyl acetate with an alcohol in the presence of a catalyst to form 2-[tris(trimethylsilyl)silyl]ethanol, then reacting it with an alkyl (meth)acrylate to form 2-[tris(trimethylsilyl)silyl]ethyl (meth)acrylate.

DESCRIPTION OF THE PREFERRED EMBODIMENT

A first step of the inventive process is to reacting 2-[tris(trimethylsilyl)silyl]ethyl acetate with an alcohol in the presence of a catalyst for ester exchange reaction to form 2-[tris(trimethylsilyl)silyl]ethanol. The alcohol used herein may be selected from among methanol, ethanol, 1-propanol and 1-butanol, though not limited thereto.

The reaction may be effected without a solvent. Solventless reaction is advantageous because extra operations such as concentration and solvent recovery are unnecessary. However, auxiliary use of a solvent is possible. The solvent, if used, is usually selected from hydrocarbons such as hexane, heptane, benzene, toluene, xylene, and cumene; and ethers such as tetrahydrofuran, di-n-butyl ether, ethylene glycol dimethyl ether, and ethylene glycol diethyl ether.

The catalyst used herein includes a variety of compounds, for example, acids such as hydrochloric acid, sulfuric acid, trifluoroacetic acid, methanesulfonic acid, benzenesulfonic acid, and p-toluenesulfonic acid; bases such as sodium methoxide, sodium ethoxide, potassium t-butoxide, and N,N-dimethylaminopyridine; salts such as sodium cyanide, potassium cyanide, sodium acetate, potassium acetate, calcium acetate, tin acetate, aluminum acetate, aluminum acetoacetate, and alumina; and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dibromide, dibutyltin dimethoxide, dibutyltin oxide, titanium tetrachloride, titanium tetrabromide, titanium (IV) methoxide, titanium (IV) ethoxide, titanium (IV) isopropoxide, and titanium (IV) oxide. They may be used alone or in admixture. Of these, Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dibromide, dibutyltin dimethoxide, dibutyltin oxide, titanium tetrachloride, titanium tetrabromide, titanium (IV) methoxide, titanium (IV) ethoxide, titanium (IV) isopropoxide, and titanium (IV) oxide are advantageous since they promote rapid reaction, resulting in higher yields. The catalyst is used in a catalytic amount and usually in an amount of 0.1 to 50 molt based on the moles of the starting reactant, 2-[tris(trimethylsilyl)silyl]ethyl acetate. An amount of 0.1 to 5 mol % is especially desirable from the standpoints of yield and cost.

Reaction is usually effected while heating the reaction system so that the low-boiling alkyl acetate resulting from ester exchange reaction, such as methyl acetate, ethyl acetate, propyl acetate or butyl acetate may be removed from the reaction system.

The resulting product, 2-[tris(trimethylsilyl)silyl]ethanol which can be purified by recrystallization. However, the 2-[tris(trimethylsilyl)silyl]ethanol in the reaction mixture has a sufficient purity for the second step, and can be employed in the next step as the mixture with the catalyst and the solvent (if any), without purification.

The second step of the inventive process is to react the 2-[tris(trimethylsilyl)silyl]ethanol resulting from the first step with a (meth)acrylate ester in the presence of a catalyst for ester exchange reaction to form 2-[tris(trimethylsilyl) silyl]ethyl (meth)acrylate. Examples of the (meth)acrylate ester used herein include methyl methacrylate, ethyl methacrylate, n-propyl methacrylate, n-butyl methacrylate, methyl acrylate, ethyl acrylate, n-propyl acrylate, and n-butyl acrylate. Of these, methyl methacrylate, ethyl methacrylate, methyl acrylate and ethyl acrylate are preferable because of their cost and rapid progress of reaction.

The reaction may be effected without a solvent. Solventless reaction is advantageous because extra operations such as concentration and solvent recovery are unnecessary. However, auxiliary use of a solvent is possible. The solvent, if used, is usually selected from hydrocarbons such as hexane, heptane, benzene, toluene, xylene, and cumene; and ethers such as tetrahydrofuran, di-n-butyl ether, ethylene glycol dimethyl ether, and ethylene glycol diethyl ether. When the solvent is used in the second step, it is economical that the solvent used in the first step is kept to the second step.

The catalyst used in the second step includes a variety of compounds, for example, acids such as hydrochloric acid, sulfuric acid, trifluoroacetic acid, methanesulfonic acid, benzenesulfonic acid, and p-toluenesulfonic acid; bases such as sodium methoxide, sodium ethoxide, potassium t-butoxide, and 4-dimethylaminopyridine; salts such as sodium cyanide, potassium cyanide, sodium acetate, potassium acetate, calcium acetate, tin acetate, aluminum acetate, aluminum acetoacetate, and alumina; and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dibromide, dibutyltin dimethoxide, dibutyltin oxide, titanium tetrachloride, titanium tetrabromide, titanium (IV) methoxide, titanium (IV) ethoxide, titanium (IV) isopropoxide, and titanium (IV) oxide. They may be used alone or in admixture. Of these, Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dibromide, dibutyltin dimethoxide, dibutyltin oxide, titanium tetrachloride, titanium tetrabromide, titanium (IV) methoxide, titanium (IV) ethoxide, titanium (IV) isopropoxide, and titanium (IV) oxide are advantageous since they promote rapid reaction, resulting in higher yields. The catalyst is used in a catalytic amount and usually in an amount of 0.1 to 50 mol % based on the moles of the intermediate, 2-[tris(trimethylsilyl)silyl]ethanol. An amount of 0.1 to 5 mol % is especially desirable from the standpoints of yield and cost. The catalyst can be newly added at the second step, although it is economical that the catalyst used in the first step is kept to the second step.

Reaction is usually effected while heating the reaction system so that the low-boiling alcohol resulting from ester exchange reaction, such as methanol, ethanol, 1-propanol or 1-butanol may be removed from the reaction system.

Since the inventive process needs no purifying operation at the end of the first step of reaction and can use a common catalyst and a common solvent, if used, in the first and second steps, a series of conversion reactions can be effected in one reactor. The possibility of one-pot reaction is of significance from the industrial aspect.

From the reaction mixture of the second step, the target compound, 2-[tris(trimethylsilyl)silyl]ethyl (meth)acrylate can be isolated in high purity and high yields by conventional distillation operation.

EXAMPLE

Examples of the invention are given for illustration, and should not be considered to be any type of limitation on the scope of the invention.

Preparation of 2-[tris(trimethylsilyl)silyl]ethyl methacrylate

Example 1

A reactor equipped with a distillation head was charged with 335 g of 2-[tris(trimethylsilyl)silyl]ethyl acetate and 2.84 g of titanium (IV) isopropoxide. The mixture was stirred and heated at 70° C. To the mixture, 100 ml of methanol was added dropwise over 2 hours, during which period the resulting methyl acetate was distilled out of the system. After 2 hours of stirring under reflux, the excess methanol was distilled off. To the residue was added 105 g of methyl methacrylate. Under reflux, the resulting methanol was distilled off. After stirring for further 2 hours, the mixture was distilled in vacuo to obtain 336 g (yield 93%) of the target compound, 2-[tris(trimethylsilyl)silyl]ethyl methacrylate.

Boiling point: 117–120° C./65 Pa

IR spectrum (liquid membrane method): νmax 2948, 2894, 1716, 1639, 1452, 1400, 1317, 1294, 1245, 1157, 939, 835, 688, 622 cm$^{-1}$ EI-mass spectrum: (m/z)$^+$=41 [(CH$_2$=C(CH$_3$))$^+$], 69 [(CH$_2$=C(CH$_3$)CO)$^+$], 259 [(M minus ethylene minus trimethylsilyl)$^+$], 287 [(M minus trimethylsilyl)$^+$], 317 [(M minus ethylene minus methyl)$^+$], 332 [(M minus ethylene)$^+$]

$^1$H-NMR spectrum (270 MHz, CDCl$_3$): δ=0.19 (s, 27H), 1.26 (m, 2H), 1.94 (m, 3H), 4.21 (m, 2H), 5.54 (m, 1H), 6.09 (m, 1H) ppm Example 2

By following the procedure of Example 1 aside from using ethyl methacrylate instead of the methyl methacrylate in Example 1, the target compound, 2-[tris(trimethylsilyl) silyl]ethyl methacrylate was obtained in a yield of 87%.

Example 3

By following the procedure of Example 1 aside from using boron tribromide instead of the titanium (IV) isopropoxide in Example 1, the target compound, 2-[tris (trimethylsilyl)silyl]ethyl methacrylate was obtained in a yield of 79%.

Example 4

By following the procedure of Example 1 aside from using aluminum isopropoxide instead of the titanium (IV) isopropoxide in Example 1, the target compound, 2-[tris (trimethylsilyl)silyl]ethyl methacrylate was obtained in a yield of 94%.

Example 5

By following the procedure of Example 1 aside from using dibutyltin oxide instead of the titanium (IV) isopropoxide in Example 1, the target compound, 2-[tris (trimethylsilyl)silyl]ethyl methacrylate was obtained in a yield of 96%.

Comparative Example 1

A mixture of 33.5 g of 2-[tris(trimethylsilyl)silyl]ethyl acetate, 270 ml of 15% aqueous sodium hydroxide and 200 ml of methanol was stirred for 4 hours at room temperature. The reaction mixture was poured into saturated aqueous sodium chloride and extracted with n-hexane. The n-hexane solution was washed, dried and concentrated, obtaining 17.6 g (yield 60%) of a crude product. On analysis by gas chromatography, it was found to contain 81.4% of 2-[tris (trimethylsilyl)silyl]ethanol and 12.7% of a mixture of three by-products, bis(trimethylsilyl)(2-hydroxyethyl)silane $HOCH_2CH_2Si(H)(Si(CH_3)_3)_2$, bis(trimethylsilyl)(2-hydroxyethyl)silanol $HOCH_2CH_2Si(OH)(Si(CH_3)_3)_2$, and 1,1-bis(trimethylsilyl)-1-(2-hydroxyethyl)-3,3,3-trimethyldisiloxane $HOCH_2CH_2Si(Si(CH_3)_3)_2(OSi(CH_3)_3)$.

To the crude product, 120 ml of methylene chloride and 8 g of triethylamine were added and stirred at 5° C. Methacryloyl chloride, 6.3 g, was added dropwise to the mixture, which was stirred for 12 hours at room temperature, poured into ice water, and extracted with ethyl acetate. The ethyl acetate solution was washed, dried and concentrated. The residue was distilled in vacuo, obtaining 15.8 g of the target compound, 2-[tris(trimethylsilyl)silyl]ethyl methacrylate. The yield throughout the two steps was 44%.

Comparative Example 2

A solution of 3.8 g lithium aluminum hydride ($LiAlH_4$) in 100 ml tetrahydrofuran was stirred at 5° C. in an argon atmosphere. To the solution, 33.5 g of 2-[tris(trimethylsilyl)silyl]ethyl acetate was added dropwise. After one hour of stirring at 5° C., with ice cooling, 3.8 ml of water, 3.8 ml of 15% aqueous sodium hydroxide, and 11.4 ml of water were successively added to the solution in the described order. The mixture was stirred for one hour at room temperature. The resulting precipitate was filtered off, and the tetrahydrofuran solution was dried and concentrated, obtaining 24.8 g of 2-[tris(trimethylsilyl)silyl]ethanol. This crude product was dissolved in a solvent and analyzed by gas chromatography, finding that it contained 98.2% of 2-[tris (trimethylsilyl)silyl]ethanol. This was esterified with methacryloyl chloride in the presence of triethylamine as the base as in Comparative Example 1. Subsequent extraction and vacuum distillation for purification gave 29.5 g of the end compound, 2-[tris(trimethylsilyl)silyl]ethyl methacrylate. The yield throughout the two steps was 82%.

Preparation of 2-[tris(trimethylsilyl)silyl]ethyl acrylate

Example 6

By following the procedure of Example 1 aside from using methyl acrylate instead of the methyl methacrylate in Example 1, the target compound, 2-[tris(trimethylsilyl)silyl] ethyl acrylate was obtained in a yield of 92%.

IR spectrum (liquid membrane method): νmax 2949, 2895, 1726, 1637, 1620, 1406, 1245, 1182, 1045, 835, 688, 623 $cm^{-1}$ EI-mass spectrum: $(m/z)^+$=55 $[(CH_2=CHCO)^+]$, 73 $[(Si(CH_3)_3)^+]$, 245 [(M minus ethylene minus trimethylsilyl)$^+$], 273 [(M minus trimethylsilyl)$^+$], 303 [(M minus ethylene minus methyl)$^+$], 318 [(M minus ethylene)$^+$].

$^1$H-NMR spectrum (270 MHz, $CDCl_3$): δ=0.19 (s, 27H), 1.25 (m, 2H), 4.22 (m, 2H), 5.80 (dd, J=10.3, 1.6 Hz, 1H), 6.10 (dd, J=17.0, 10.3 Hz, 1H) 6.40 (dd, J=17.0, 1.6 Hz, 1H) ppm By starting with 2-[tris(trimethylsilyl)silyl]ethyl acetate, the inventive process is successful in preparing 2-[tris (trimethylsilyl)silyl]ethyl (meth)acrylate in high yields on an industrial scale.

Japanese Patent Application No. 2000-000888 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

What is claimed is:

1. A process for preparing 2-[tris(trimethylsilyl)silyl]-ethyl (meth)acrylate, comprising the steps of reacting 2-[tris (trimethylsilyl)silyl]ethyl acetate with an alcohol in the presence of a catalyst to form 2-[tris(trimethylsilyl)-silyl] ethanol, then reacting the 2-[tris(trimethylsilyl)-silyl]ethanol with a (meth)acrylate to form 2-[tris(trimethylsilyl)silyl] ethyl (meth)acrylate.

2. The process of claim 1 wherein the catalyst is a Lewis acid.

3. The process of claim 1 wherein the catalyst is a Lewis acid containing Al, B, Sn or Ti.

4. The process of claim 1, wherein the alcohol is methanol, ethanol, 1-propanol or 1-butanol.

5. The process of claim 1, wherein the catalyst is an acid, base, a salt, or a Lewis acid.

6. The process of claim 1, wherein the catalyst is hydrochloric acid, sulfuric acid, trifluoroacetic acid, methanesulfonic acid, benzenesulfonic acid, p-toluenesulfonic acid, sodium methoxide, sodium ethoxide, potassium t-butoxide, N,N-dimethylaminopyridine, sodium cyanide, potassium cyanide, sodium acetate, potassium acetate, calcium acetate, tin acetate, aluminum acetate, aluminum acetoacetate, alumina, aluminum trichloride, aluminum ethoxide, aluminum isopropoxide, boron trifluoride, boron trichloride, boron tribromide, tin tetrachloride, tin tetrabromide, dibutyltin dichloride, dibutyltin dibromide, dibutyltin dimethoxide, dibutyltin oxide, titanium tetrachloride, titanium tetrabromide, titanium (IV) methoxide, titanium (IV) ethoxide, titanium (IV) isopropoxide, or titanium (IV) oxide or mixtures thereof.

7. The process of claim 2, wherein the Lewis acid is aluminum trichloride, aluminum ethoxide, aluminum isopropoxide, boron trifluoride, boron trichloride, boron tribromide, tin tetrachloride, tin tetrabromide, dibutyltin dichloride, dibutyltin dibromide, dibutyltin dimethoxide, dibutyltin oxide, titanium tetrachloride, titanium tetrabromide, titanium (IV) methoxide, titanium (IV) ethoxide, titanium (IV) isopropoxide, or titanium (IV) oxide.

8. The process of claim 1, wherein the amount of catalyst is 0.1 to 50 mol % based on the moles of 2-[tris (trimethylsilyl)silyl]ethyl acetate.

9. The process of claim 8, wherein said amount is 0.1 to 5 mol %.

10. The process of 1, wherein the (meth) acrylate which is reacted with 2-[tris (trimethylsilyl)-silyl]ethanol is methyl methacrylate, ethyl methacrylate, n-propyl or n-butyl acrylate.

11. The process of claim 1, wherein the (meth) acrylate which is reacted with 2- [tris(trimethylsilyl)-silyl]ethanol is methyl methacrylate, ethyl methacrylate, methyl acrylate or ethyl acrylate.

* * * * *